(12) United States Patent
Stone

(10) Patent No.: US 7,711,436 B2
(45) Date of Patent: May 4, 2010

(54) MEDICAL DEVICE ELECTRICAL LEAD DESIGN FOR PREVENTING TRANSMITTANCE OF UNSAFE CURRENTS TO A PATIENT

(75) Inventor: Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 33 days.

(21) Appl. No.: 11/739,386

(22) Filed: Apr. 24, 2007

(65) Prior Publication Data
US 2008/0221568 A1 Sep. 11, 2008

Related U.S. Application Data

(60) Provisional application No. 60/894,135, filed on Mar. 9, 2007.

(51) Int. Cl.
*A61N 1/00* (2006.01)
(52) U.S. Cl. .......................................... 607/63; 607/116
(58) Field of Classification Search .................. 607/63, 607/115, 116
See application file for complete search history.

(56) References Cited

U.S. PATENT DOCUMENTS

| | | | |
|---|---|---|---|
| 4,907,589 A | 3/1990 | Cosman | |
| 5,209,233 A | 5/1993 | Holland | |
| 5,433,732 A | 7/1995 | Hirschberg | |
| 5,476,485 A | 12/1995 | Weinberg et al. | |
| 6,132,426 A | 10/2000 | Kroll | |
| 6,209,764 B1 | 4/2001 | Hartlaub et al. | |
| 6,421,567 B1 | 7/2002 | Witte | |
| 6,662,048 B2 | 12/2003 | Balczewski et al. | |
| 6,892,095 B2 | 5/2005 | Salo | |
| 6,944,489 B2 | 9/2005 | Zeijlemaker et al. | |
| 7,047,074 B2 | 5/2006 | Connelly et al. | |
| 2003/0013948 A1 | 1/2003 | Russell | |
| 2003/0125774 A1 | 7/2003 | Salo | |
| 2003/0167081 A1 | 9/2003 | Zhu et al. | |
| 2006/0111706 A1 | 5/2006 | Truckai et al. | |
| 2006/0231807 A1* | 10/2006 | Tosaka et al. | ................ 252/500 |
| 2006/0247684 A1 | 11/2006 | Halperin | |

OTHER PUBLICATIONS

International Search Report, International Application No. PCT/US2007/067309, Feb. 12, 2008.
Written Opinion of the International Searching Authority, International Application No. PCT/US2007/067309, Feb. 12, 2008.

* cited by examiner

*Primary Examiner*—Scott M Getzow

(57) ABSTRACT

An electrical lead including a conductor assembly, an electrode, and a thermally sensitive material. The conductor assembly has one or more conductors. The electrode is in electrical communication with one of the conductors and has an outer contact adapted for contacting adjacent body tissue of a patient. The thermally sensitive material is electrically connected between the one conductor and the electrode outer contact, and is configured to exhibit high impedance in the presence of currents considered unsafe to the patient, thereby preventing the unsafe currents from flowing through the thermally sensitive material and through the electrode outer contact potentially causing the adjacent body tissue to increase in temperature to an unsafe level. The unsafe currents cause the thermally sensitive material to increase in temperature, thereby causing the material to transition to a high impedance state.

30 Claims, 7 Drawing Sheets

MEDICAL DEVICE ELECTRICAL LEAD DESIGN FOR PREVENTING TRANSMITTANCE OF UNSAFE CURRENTS TO A PATIENT

CROSS-REFERENCE TO RELATED APPLICATION

The present application claims priority to U.S. provisional patent application filed Mar. 9, 2007 and assigned Ser. No. 60/894,135, the entire disclosure of which is incorporated herein by reference.

FIELD

The present invention relates generally to medical devices, and, more particularly, relates to designs for medical device electrical leads extending between the medical devices and the patient.

BACKGROUND

Since the introduction of the first implantable pacemakers in the 1960s, there have been considerable advancements in both the fields of electronics and medicine, such that there is now a wide assortment of commercially available body-implantable electronic medical devices. This class of implantable medical devices (IMDs) generally includes therapeutic and diagnostic devices, such as pacemakers, cardioverter/defibrillators, hemodynamic monitors, neural stimulators, and drug administering devices, as well as other devices for alleviating the adverse effects of various health ailments.

As is known, modern electrical therapeutic and diagnostic devices for the heart and/or other areas of the body generally include an electrical connection between the device and a patient's body. This connection is usually provided by at least one medical electrical lead, which is typically implanted (at least partially) within the patient's body. For example, a neural stimulator delivers mild electrical impulses to neural tissue using one or more electrical leads. Such neural stimulation often results in pain relief or a reduction in tremors depending on where the electrodes are placed. Each electrical lead used with such devices typically takes the form of a long, generally straight, flexible, insulated set of conductors. At its proximal end, the lead is typically connected to a connector of the device, which also may be implanted within the patient's body. Generally, one or more electrodes are located at or near the distal end of the lead and are attached to, or otherwise come in contact with, the patient's body. Such devices may be controlled by a physician or the patient through the use of an external programmer.

Other advancements in medical technology have led to improved imaging technologies, e.g., magnetic resonance imaging (MRI). As further described below with respect to its process, MRI is an anatomical imaging tool which utilizes non-ionizing radiation (i.e., no x-rays or gamma rays) and provides a non-invasive method for the examination of internal structure and function. In particular, MRI permits 3-D imaging of soft tissue better than any other imaging method. During the MRI imaging sequence, a radio-frequency field is applied to the patient. Magnetic resonance spectroscopic imaging (MRSI) systems are also known and are herein intended to be included within the terminology "MRI" systems or scanners.

Further, shortwave diathermy, microwave diathermy, ultrasound diathermy, and the like have been shown to provide therapeutic benefits to patients, such as to relieve pain, stiffness, and muscle spasms; to reduce joint contractures; to reduce swelling and pain after surgery; to promote wound healing; and the like. Generally, in using such diathermy apparatuses, energy (e.g., short-wave energy, microwave energy, ultrasound energy, or the like) is directed into a localized area of the patient's body.

Traditionally, use of the above-described technologies have been discouraged for patients having IMDs, as the environment produced by the MRI or diathermy apparatuses is generally considered hostile to such IMDs. As is known, the energy fields, generated during the MRI or diathermy processes, have potential for inducing an electrical current within leads of IMDs as well as leads of other medical devices located within the patient. In conventional leads, this electrical current is typically conducted into tissue adjacent to the ends of the lead. Because the tissue area adjacent to the electrodes is often very small, the current conducting through this adjacent tissue results in the tissue heating. This may result in tissue damage when the currents are too large.

Thus, what are needed are medical device electrical lead systems that reduce tissue heating to levels that do not induce tissue damage.

BRIEF SUMMARY OF THE INVENTION

In one embodiment, an electrical lead is provided. The electrical lead includes a conductor assembly, an electrode, and a thermally sensitive material. The conductor assembly has one or more conductors. The electrode is in electrical communication with one of the conductors and has an outer contact adapted for contacting adjacent body tissue of a patient. The thermally sensitive material is electrically connected between the one conductor and the electrode outer contact, and is configured to exhibit high impedance in the presence of currents considered unsafe to the patient, thereby preventing the unsafe currents from flowing through the thermally sensitive material and through the electrode outer contact potentially causing the adjacent body tissue to increase in temperature to an unsafe level. The unsafe currents cause the thermally sensitive material to increase in temperature, thereby causing the material to transition to a high impedance state.

In another embodiment, an electrode is provided. The electrode includes an outer contact, an inner contact, and a thermally sensitive material. The outer contact is adapted for contacting adjacent body tissue of a patient. The inner contact is adapted for electrical coupling to a lead conductor. The thermally sensitive material is electrically connected between the inner contact and the outer contact, and is configured to exhibit high impedance in the presence of currents considered unsafe to the patient, thereby preventing the unsafe currents from flowing through the thermally sensitive material and through the outer contact potentially causing the adjacent body tissue to increase in temperature to an unsafe level. The unsafe currents cause the thermally sensitive material to increase in temperature, thereby causing the material to transition to a high impedance state.

DETAILED DESCRIPTION OF THE PREFERRED EMBODIMENTS

Figure 1:
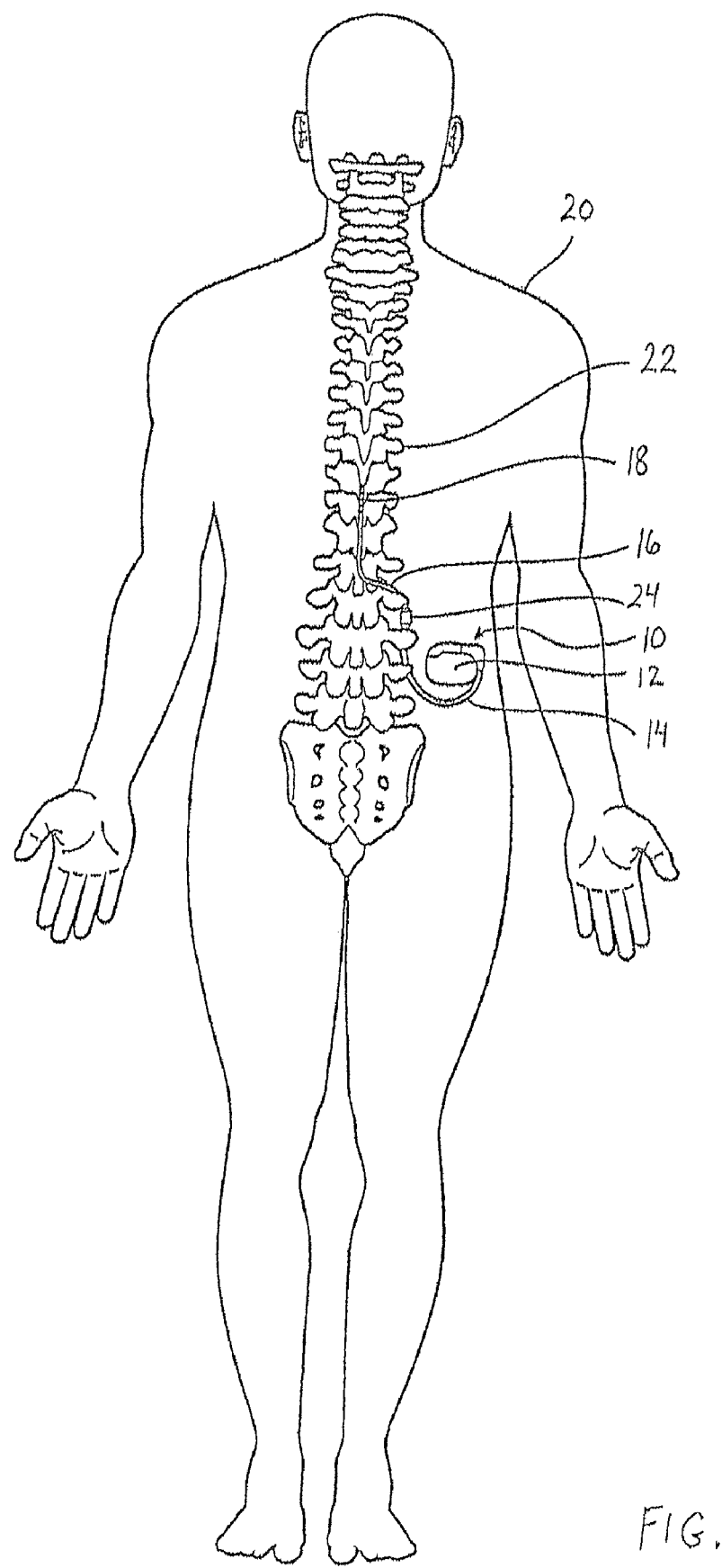
FIG. 1 is a perspective view of an exemplary IMD as provided in a patient in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Embodiments of the invention relate to implanted devices, and specifically relate to designs for medical device electrical leads extending between the implanted device and the electrodes of the implanted leads. In particular, the lead designs are configured for preventing unsafe currents from being conducted through the electrode and into the tissue of the patient. Embodiments described and illustrated herein pertain to implantable medical devices (IMDs); however, the invention can extend to any lead-bearing medical device, whether implantable or not. Furthermore, while the embodiments provided herein relate to certain IMDs, it should be appreciated that such embodiments are exemplary in nature. As such, the invention is not limited to any particular IMD, but instead is applicable to any IMD, including therapeutic and diagnostic devices, such as pacemakers, cardioverter/defibrillators, hemodynamic monitors, neurostimulators, and drug administering devices, as well as other devices for alleviating the adverse effects of various health ailments.

FIG. 1 illustrates an exemplary IMD in accordance with certain embodiments of the invention. The IMD 10 shown is a typical spinal cord stimulation (SCS) system and includes a pulse generator such as a SCS neurostimulator 12, a lead extension 14 having a proximal end coupled to the neurostimulator 12, and a lead 16 having a proximal end coupled to a distal end of the extension 14 and having a distal end coupled to one or more electrodes 18. The neurostimulator 12 is typically placed in the abdomen of a patient 20, and the lead 18 is placed somewhere along the patient's spinal cord 22. While only shown with a single lead 18, it is to be appreciated that the IMD 10, in certain embodiments, can have a plurality of leads. Such a system may also include a physician programmer and a patient programmer (not shown).

The neurostimulator 12 may be considered to be an implantable pulse generator and capable of generating multiple pulses or other electrical waveforms. While the neurostimulator 12 typically provides electrical stimulation by way of pulses, other forms of stimulation may be used such as continuous electrical stimulation.

The lead 16 includes one or more insulated electrical conductors each coupled at their proximal end to a connector 24 and to the electrodes 18 (or contacts) at its distal end. As is known, some leads are designed to be inserted into a patient percutaneously and some are designed to be surgically implanted. In certain embodiments, the lead 16 may contain a paddle at its distant end for housing the electrodes 18. In alternate embodiments, the electrodes 20 may comprise one or more ring contacts at the distal end of the lead 16.

While the lead 16 is shown as being implanted in position to stimulate a specific site in the spinal cord 22, it could also be positioned along the peripheral nerve or adjacent neural tissue ganglia or may be positioned to stimulate muscle tissue. Furthermore, electrodes 18 (or contacts) may be epidural, intrathecal or placed into spinal cord 22 itself. Effective spinal cord stimulation may be achieved by any of these lead placements. While the lead connector at proximal end of the lead 16 may be coupled directly to the neurostimulator 12, the lead connector is typically coupled to the lead extension 14 as is shown in FIG. 1.

Figure 2:
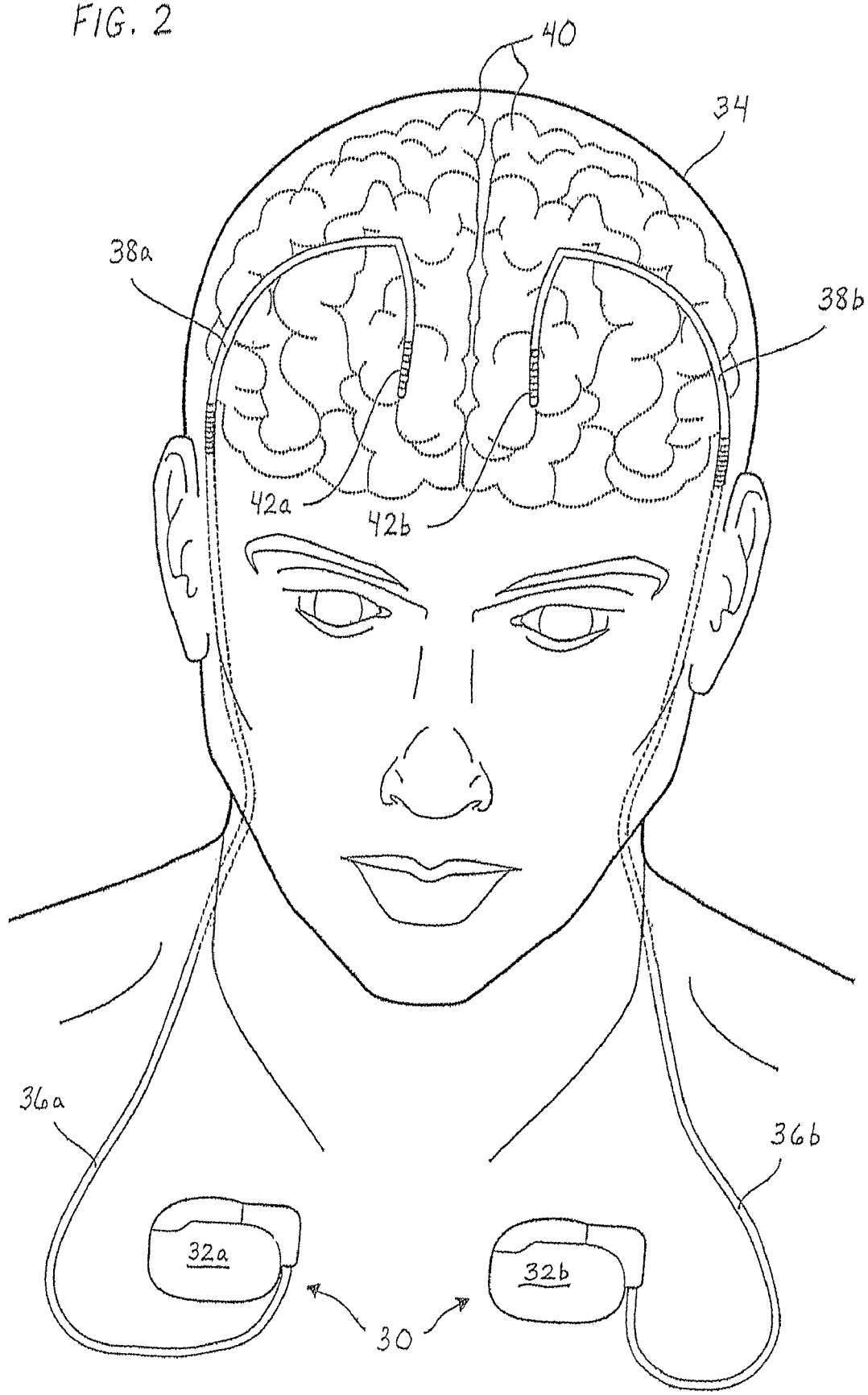
FIG. 2 is a perspective view of another exemplary IMD as provided in a patient in accordance with certain embodiments of the invention.

FIG. 2 illustrates another exemplary IMD in accordance with certain embodiments of the invention. The IMD 30 shown is a typical deep brain stimulation (DBS) system and includes substantially the same components as does an SCS; that is, at least one neurostimulator, at least one extension, and at least one stimulation lead containing one or more electrodes. As can be seen, each neurostimulator 32a and 32b is implanted in the pectoral region of patient 34. Corresponding extensions 36a and 36b are deployed up through the patient's neck, and corresponding leads 38a and 38b are implanted in the patient's brain 40 as is shown at 42a and 42b. As can be seen, each of the leads 38 is connected to its respective extension 36 just above the ear on both sides of the patient 34.

Figure 3:
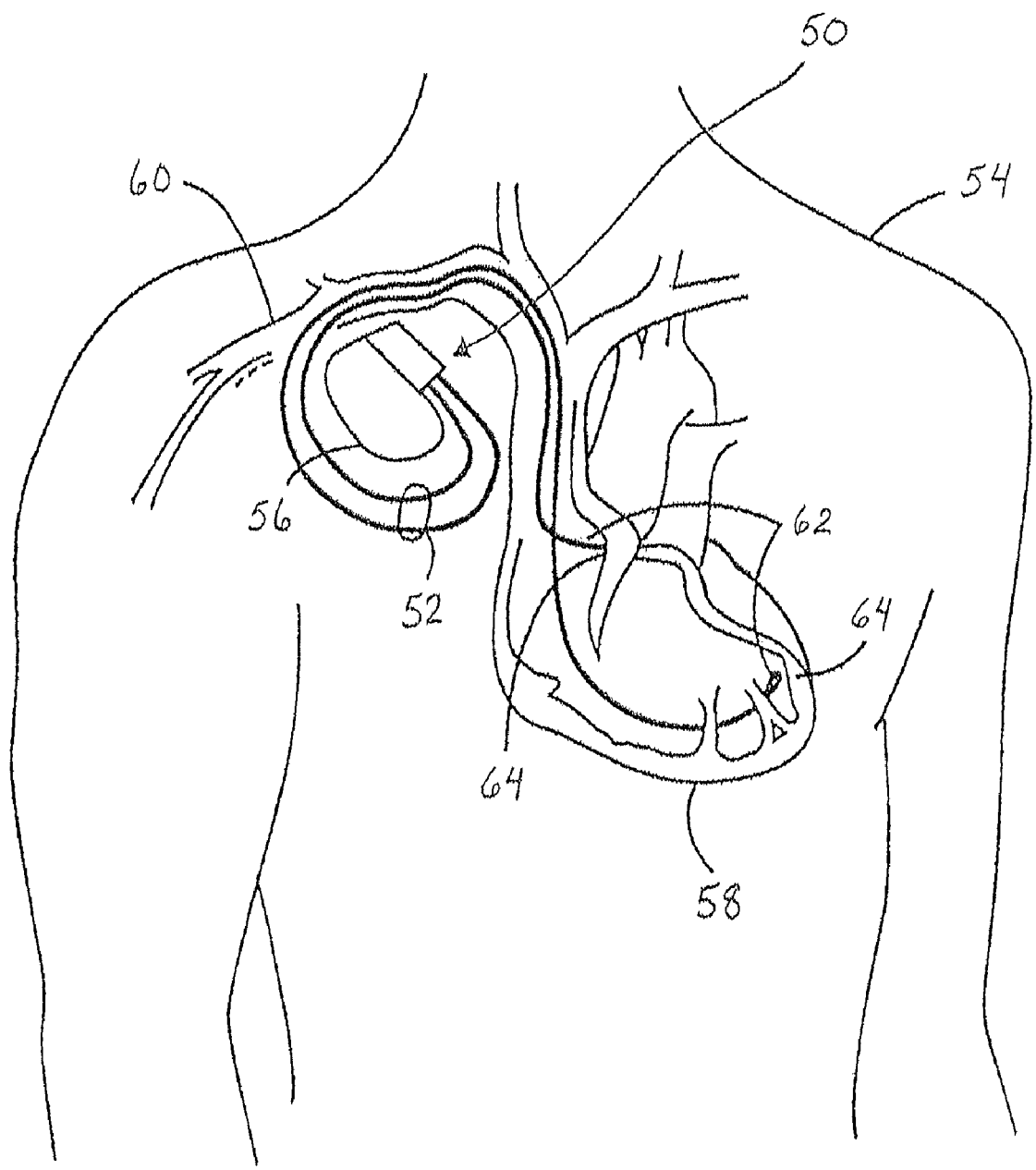
FIG. 3 is a perspective view of a further exemplary IMD as provided in a patient in accordance with certain embodiments of the invention.

FIG. 3 illustrates a further exemplary IMD in accordance with certain embodiments of the invention. The IMD 50 is a cardiac medical device, exemplarily shown as a pacemaker, and includes one or more leads 52 implanted in a patient 54. The leads 52 extend from the pacemaker can 56 and lead into the patient's heart 58 via a vein 60. Located generally near distal ends 62 of the leads 52 are one or more exposed conductive electrodes 64 that are attached to the heart tissue for sensing cardiac activity, delivering electrical pacing stimuli, and/or providing a cardioversion/defibrillation shock to the heart 58. The contact area between the electrodes 64 and the tissue of the heart 58 may be very small as compared, for example, to the contact area between the IMD 50 and the patient's body.

To date, there have been many designs with respect to medical device electrical leads, such as the implantable leads of the IMDs exemplified in FIGS. 1-3 as well as implantable leads of other medical devices, so as to limit the penetration therein of significant alternating electromagnetic fields and/or radio-frequency energy. In particular, a variety of different coverings have been used for such leads to provide such protection. However, it has been found that most of these coverings do not adequately protect tissue from heating. In turn, there continues to be potential for currents being induced within the lead conductors (from such fields) which can cause thermal damage to patient tissue. As described above, these induced currents can be found to be harmful to the patient. In addition, events other than the above-described induced current phenomenon can be sources for currents which can also be harmful to the patient. For example, such events can stem from medical device equipment failure, defective medical device, etc. As such, a variety of lead designs have been taught, to be used solely or in combination with the lead shield coverings, so as to prevent the passage of harmful electric currents to the patient from one or more of the events described above.

For example, a number of lead designs have been taught to specifically protect the patient from potential detrimental effects of unsafe currents induced from electromagnetic fields. In some cases, the lead designs involve additional circuitry so as to provide further electrode paths for the induced current. In turn, the heat brought to the tissue from the dissipating current is spread over a larger portion of tissue, thereby decreasing the likelihood of tissue damage from any one area of tissue being exposed to the current. In related cases, the lead designs are configured to separate the higher frequency induced currents from the lower frequency therapy signals (e.g., for pacing, stimulation, sensing, and the like) signals. As a result, filtering of the induced currents is achieved, while not interfering with the normal functioning of the medical device. In further lead designs, use of passive and/or active electronic components are provided within the lead circuit to prevent or at least limit unsafe currents being induced from electromagnetic fields and/or stemming from other events, as exemplified above. For example, lead designs employing passive components, specifically inductors, have been taught so as to function in attenuating the high frequencies of magnetic signals generally used for MRI. Alternatively, lead designs employing active components have been taught so as to limit current flow upon detection of a predetermined physiological detection. For example, such designs can involve detection of electromagnetic fields in a predetermined frequency range (via a sensor), followed by activation of a CMOS Field Effect Transistor (FET) within the lead body so as to open the lead connection to the electrode.

The above lead designs have been shown to have varying degrees of effectiveness; however, all can have drawbacks. For example, by using additional circuitry and/or electrical components, there is increased cost in manufacturing the lead as well as increased sources for lead failure. Additionally, the control inputs to such devices can also be affected by these fields. As such, they are limited with respect to their application in protecting the patient due to other events causing unsafe currents, including medical device equipment failure, defective medical device, etc.

A number of lead designs have been taught that are more universally applicable with respect to preventing or limiting unsafe currents, regardless of whether they are induced from electromagnetic fields and/or radio-frequency energy or are the result of other events causing unintended unsafe currents, as exemplified above. Specifically, these lead designs are designed to include electronic components that are generally passive, similar to that already described above with respect to use of an inductor. In turn, based on the magnitude of what is sensed, the device is configured to automatically respond to modify its output. Some of these devices have involved those designed for current stoppage, such as micro-sized fuses or circuit breakers, and are geared to interrupt the electrical connection to the corresponding electrodes upon unsafe current being sensed by the current stoppage devices. Other devices have involved those designed to limit current. In particular, a diode has been taught to be used. For example, diodes are commercially available which would block current exceeding certain current levels.

However, once again, these lead designs have limitations. For example, with respect to the current stoppage devices, once tripped, such leads can no longer facilitate monitoring or therapy functionality. As such, while the devices enable the current to be entirely prevented from flowing to the patient, if the patient warranted diagnosis or therapy from the lead following such device being tripped, there would be little recourse without first replacing components within the devices (as in the case of fuses) or resetting the devices (as in the case of circuit breakers). With respect to the current limiting designs, the device can be used following a high voltage event without replacement of components of the device or resetting of the device. However, such a lead design still allows for current, even at reduced levels, to pass to the patient via the electrode during such high voltage events.

Thus, embodiments of the invention involve lead systems that function in limiting the passage of unsafe electric currents through a medical electrode attached to a patient, while further overcoming one or more of the limitations facing the lead designs taught to date. In particular, the lead systems provide such functionality using a limited amount of additional materials, while also being widely applicable so as to be used for unsafe currents which are induced from electromagnetic fields or stem from other events, as exemplified above. In addition, these lead systems limit current to safe levels while still enabling normal operation of the lead system after MRI or other unsafe events without requiring maintenance of the lead system.

Figure 4:
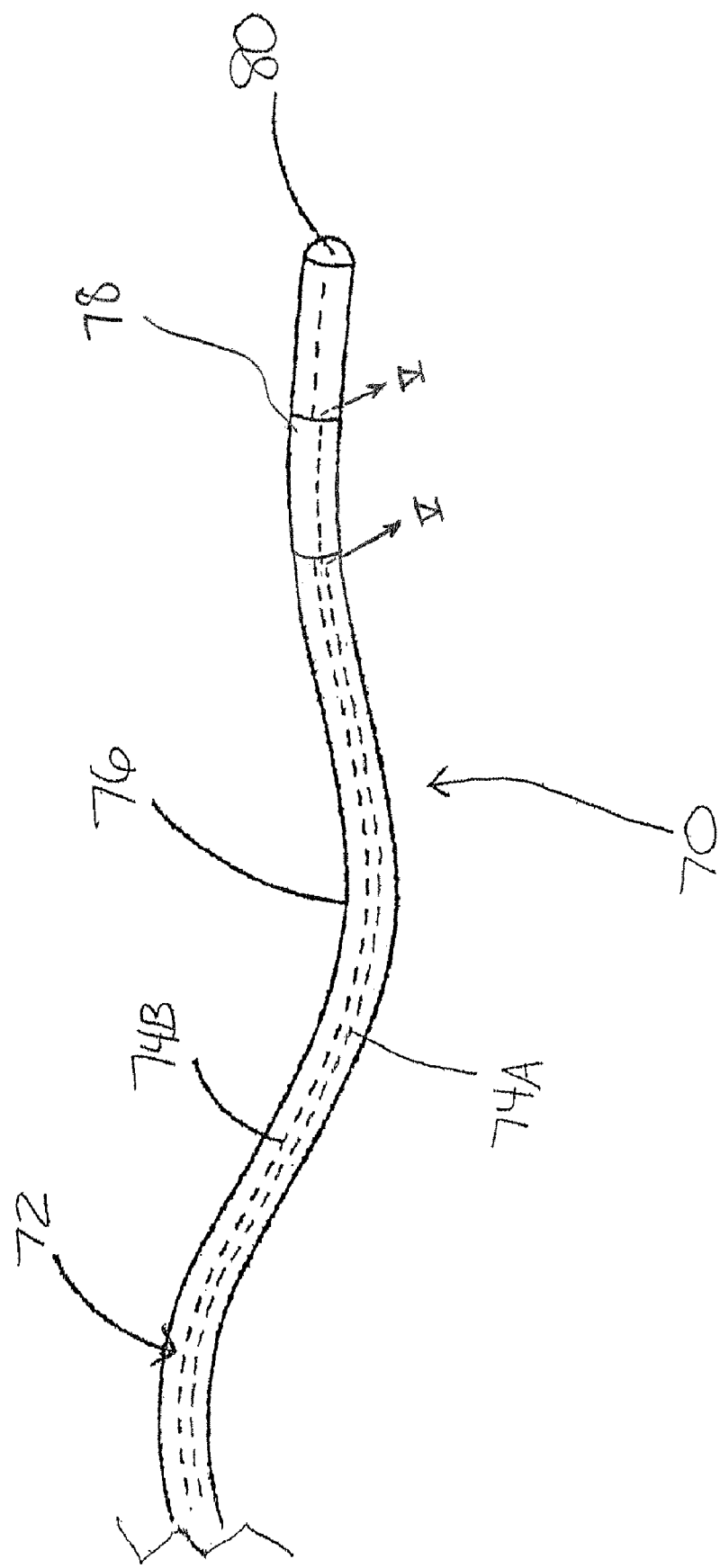
FIG. 4 is a perspective view of a medical device electrical lead in accordance with certain embodiments of the invention.

FIG. 4 illustrates an enlarged view of a distal end of a medical device electrical lead in accordance with certain embodiments of the invention. As shown, the electrical lead 70 includes a conductor assembly 72 having one or more conductors (e.g., such as conductors 74a and 74b as shown) covered by an insulating layer 76. As should be appreciated, the conductors 74a and 74b are insulated from each other within the conductor assembly 72. Each of the conductors 74a and 74b is in electrical communication with at least one electrode (e.g., such as a ring electrode 78 or a tip electrode 80, as respectively shown). As described above, the electrical lead 70 would function in electrically coupling a medical device (such as IMDs 10, 30, and 50 of FIGS. 1, 2, and 3, respectively) to the electrodes 78 and 80. Furthermore, the electrodes 78 and 80 of the lead 70 are placed adjacent or proximate to the patient's body tissue (as exemplified in FIGS. 1-3) so as to enable the sensing and/or therapy functioning of the medical device.

While not visibly shown in FIG. 4, a thermally sensitive material (exemplarily illustrated in FIG. 5 and referenced as 82) is electrically connected to each of the conductors 74a and 74b. The thermally sensitive material 82 is positioned in electrical series between the conductors 74a and 74b and their respective electrodes 78 and 80. As such, the material 82 forms the only conductive path from the conductors 74a and 74b to their respective electrodes 78 and 80. As will be described below, the thermally sensitive material 82, in the presence of unsafe current on the conductors 74a or 74b, transitions to a high impedance state, thereby limiting the current flowing into the patient to be only at safe levels. In certain embodiments, the material 82 is positioned just before the electrodes 78 and 80 so as to prevent unsafe currents from being induced within the section of the conductors which connect from the material 82 to the electrodes 78 and 80. In certain embodiments, as further illustrated in FIG. 5 and described below, the material 82 is integrated in an assembly with each of the electrodes 78 and 80; however, the invention should not be limited to such. For example, the material 82 can be electrically connected to the electrodes 78 and 80 of the lead 70, while being physically separated from the electrodes 78 and 80.

Figure 5:
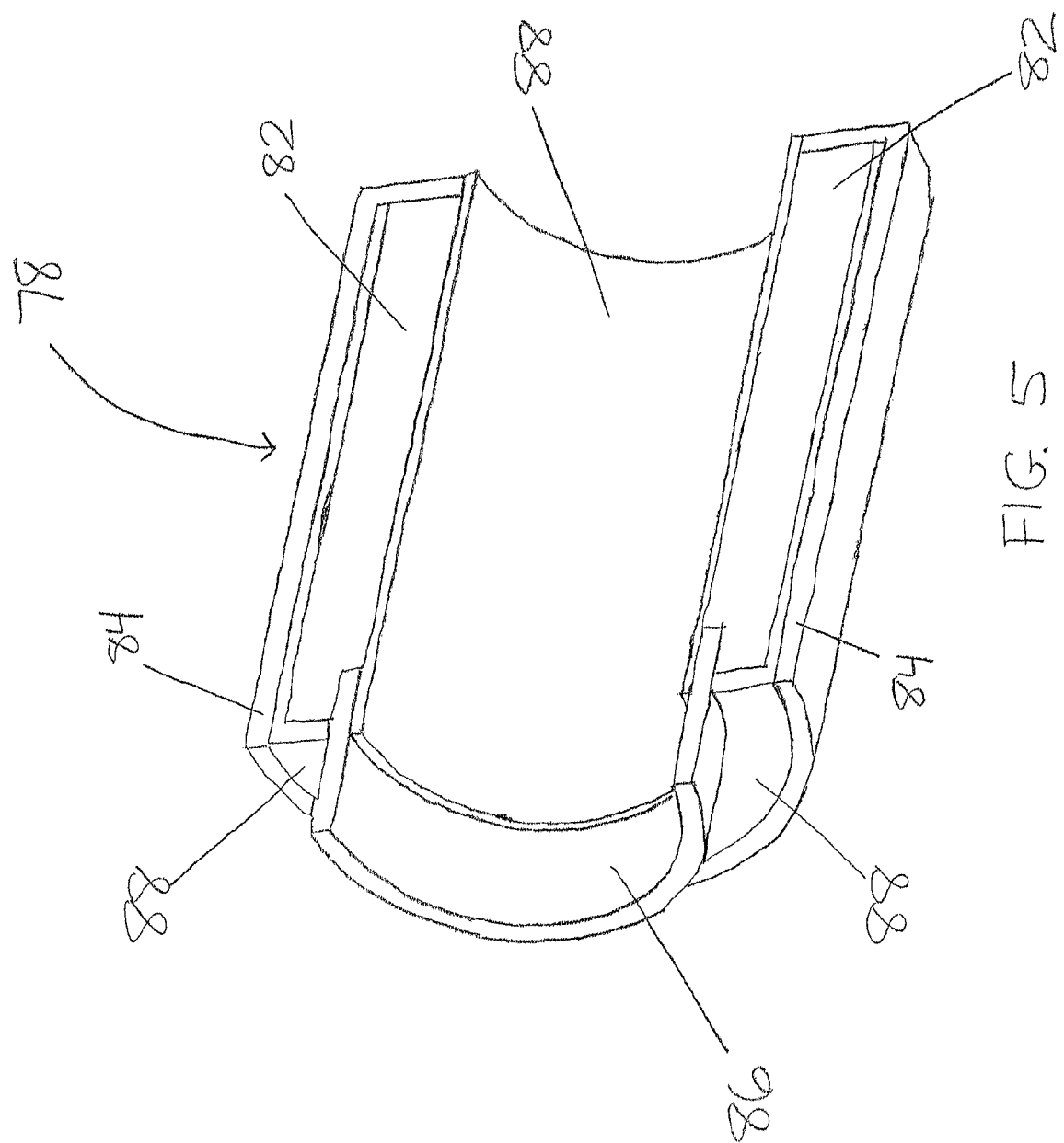
FIG. 5 is a cross sectional view of a ring electrode of the medical device electrical lead of FIG. 4, taken along the lines V-V in accordance with certain embodiments of the invention.

FIG. 5 shows a cross-sectional view of the ring electrode 78 of the medical device electrical lead 70 of FIG. 4, taken along the lines V-V. As illustrated, FIG. 5 is an axial slice of the ring electrode 78 only; as such, the conductors 74a and 74b and the insulating layer 76 are not shown in the view. In particular, the view illustrates a cross section of the ring electrode 78 starting from a proximal portion of the electrode 78 and extending to a distal end of the electrode 78. As described above with reference to FIG. 4, in certain embodiments, the thermally sensitive material 82 can be integrated with the ring electrode 78, thereby forming an assembly. In certain embodiments, as shown, the thermally sensitive material 82 is provided as a tube-shaped structure; however, the invention should not be limited to such. Instead, the material 82 can be provided as any of a wide variety of different structures (e.g., rings, plates, strips, etc.). In certain embodiments, the material 82 is sized so as to be internally positioned, at least in part, within an outer contact 84 of the ring electrode 78.

As shown, the material 82 is electrically connected to the outer contact 84. This connection between the material 82 and the contact 84 can be provided directly (as exemplarily shown) or indirectly (e.g., via at least one further contact electrically joining the material 82 and the contact 84). In certain embodiments, as shown, the distal end portions of both the material 82 and the contact 84 are positioned so as to be in electrical contact with each other; however, the point(s) of electrical contact between the material 82 and the contact 84 can be varied as desired.

The material 82 is further electrically connected to the corresponding conductor 74a of the lead 70 (shown in FIG. 4). Similar to that described above, this connection between the material 82 and the conductor 74a can be provided directly or indirectly (via at least one inner contact 86, such as the exemplarily shown weld ring). The inner contact 86 can include any of a variety of different structures. While not shown in FIG. 5, a distal end portion of the lead conductor 74a for the ring electrode 78 would be electrically connected to the inner contact 86 (e.g., via a weld joint). In turn, the inner contact 86 would be electrically connected to the material 82, thereby completing the conductive path from the conductor 74a to the material 82 (via the inner contact 86). In certain embodiments, as shown, a distal end portion of the inner contact 86 and a proximal end portion of the material 82 are positioned so as to be in electrical contact with each other, thereby completing the above-mentioned conductive path; however, the point(s) of electrical contact between the contact 86 and the material 82 can be varied to comply with other design requirements.

As should be appreciated, the outer and inner contacts 84, 86 are formed of electrically conductive material, e.g., metal (such as a single metal or a combination of any of a plurality of metals). As described above, in certain embodiments, the distal end portions of both the thermally sensitive material 82 and the outer contact 84 are positioned so as to be in electrical contact with each other. As further described above, in certain embodiments, a distal end portion of the inner contact 86 and a proximal end portion of the material 82 are positioned so as to be in electrical contact with each other. As should be appreciated, these electrical connections enable a conductive path being established across a substantial portion of the material 82 for currents to flow from the lead conductor 78a to the outer contact 84 of the electrode 78. As such, with these electrical connections, the potential for unsafe currents to arc between the contacts inner contact 86 and the outer contact 84 is restricted, thereby preventing unsafe currents from bypassing the corresponding high impedance pathway through the thermally sensitive material 82.

As illustrated, the ring electrode assembly further includes an insulating material 88. The insulating material 88 can be formed of any of a variety of non-conducting materials, such as glass or plastic. As shown, the insulating material 88 surrounds (e.g., coats) the thermally sensitive material 82 except for the locations in which the outer contact 84 and the inner contact 86 are in electrical contact with thermally sensitive material 82. For example, in certain embodiments, as shown, the insulating material 88 is limited in its coverage of the thermally sensitive material 82 at its distal end (so as to facilitate electrical connection between the material 82 and the outer contact 84) as well as at its proximal end (so as to facilitate electrical connection between the material 82 and the inner contact 86). As FIG. 5 shows, the thermally sensitive material 82 is completely encased within the electrode 78.

The inclusion of the insulating material 88 serves at least two functions for the electrode assembly. First, the material 88 generally serves to hermetically seal the thermally insulating material 82 within the assembly. Second, the material serves to prevent high currents from arcing from the lead conductor 74a (via the inner contact 86) directly to the outer contact 84. As shown, by surrounding a majority of the thermally sensitive material 82, the insulating material 88 further fills in the voids between the inner contact 86 and the outer contact 84. In turn, the high currents are further restrained from arcing between the inner contact 86 and the outer contact 84, thereby restricting currents from bypassing the electrical pathway through the thermally sensitive material 82.

While FIG. 5 illustrates a lead design with the thermally sensitive material 82 forming an assembly with the ring electrode 78, it should be appreciated that such material 82 can also be likewise incorporated with other electrodes (such as the tip electrode 80) in forming lead designs having similar current limiting functionality. One skilled in the art would understand the configuration of these similar designs based on FIG. 5 and the corresponding description above. For example, if the thermally sensitive material 82 were formed with a tip electrode, the outer contact of the electrode, instead of being formed as a ring around the electrical lead, would be affixed at the lead end. Similar to that described above and shown for the ring electrode 78 of FIGS. 4 and 5, the thermally sensitive material 82 would be sized so as to be internally positioned, at least in part, within the outer contact of the tip electrode. Further, the material 82 would be surrounded (e.g., coated) by insulating material (e.g., such as the insulating material 88 shown in FIG. 5) except for electrical junction points, facilitating electrical connection with a conductor of the electrical lead and further electrical connection with the outer contact of the tip electrode. Another example may involve an electrode having two or more segmented outer contacts. This would be similar to the above-described tip electrode configuration, but instead of being affixed at the lead end, the segmented outer contacts would generally be located in one or more different locations over the length of the lead. In such case, the thermally sensitive material 82 would be accordingly sized and internally positioned (at least in part) to each of the segmented outer contacts. Further, the material 82 at each outer contact would be surrounded (e.g., coated) by insulating material (e.g., such as the insulating material 88 shown in FIG. 5) except for electrical junction points, facilitating electrical connection with a conductor of the electrical lead and further electrical connection with the corresponding segmented outer contact of the tip electrode.

The above examples describe but two further electrodes that can be configured with the thermally sensitive material 82. As should be appreciated and as demonstrated through the use of the above examples, one skilled in the art should be sufficiently equipped from what has been already described and illustrated with respect to the ring electrode 78 of FIGS. 4 and 5 to apply these teachings in further varieties of electrodes commercially available now and in the future.

Figure 6:
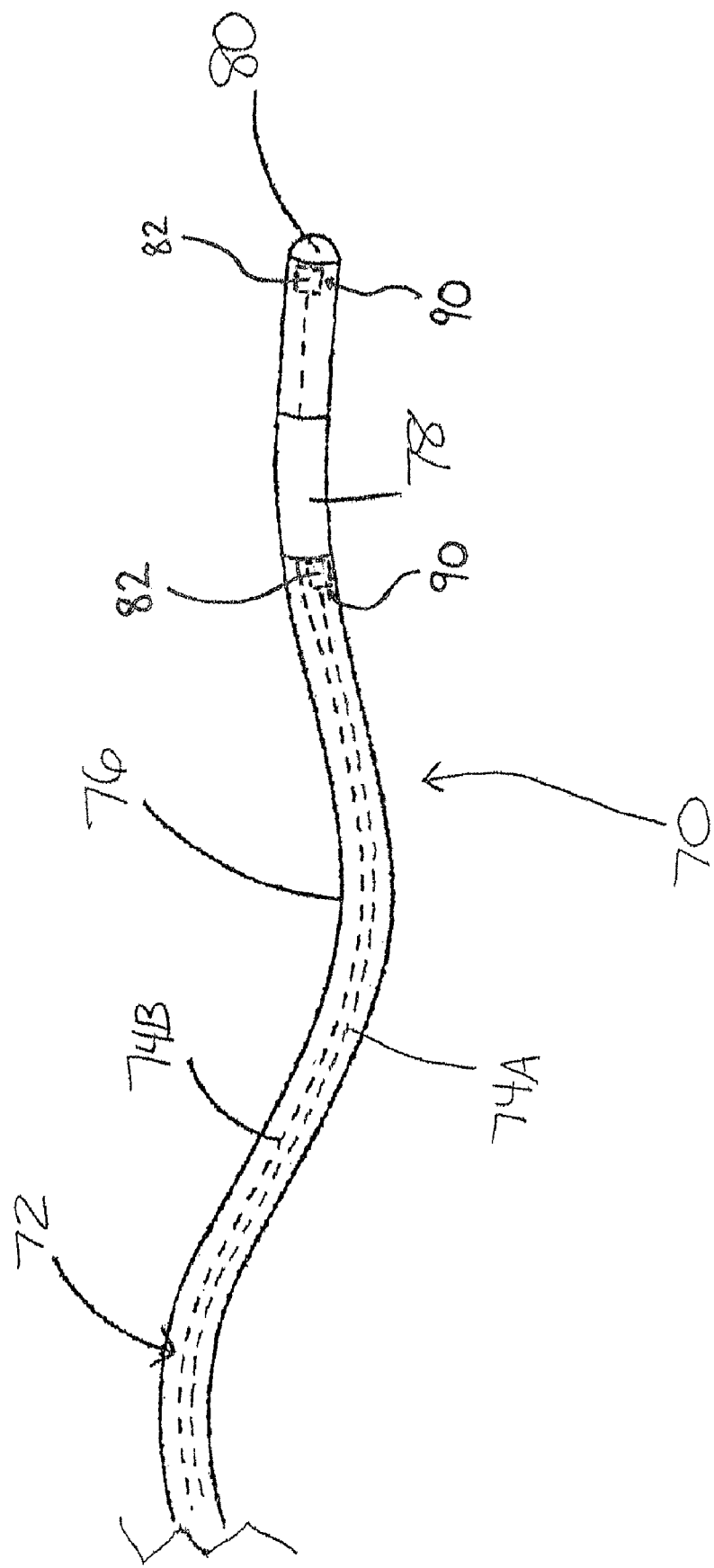
FIG. 6 is a perspective view of the medical device electrical lead of FIG. 4 in accordance with certain embodiments of the invention.

Additionally, in contrast to the lead design of FIG. 5, whereby the thermally sensitive material 82 is integrated with the ring electrode 78 to form an assembly, it is further described herein that the material 82 can be separately located outside yet proximate to the ring electrode 78 (and tip electrode 80). As such, in certain embodiments, the material 82 is electrically connected between the lead conductor 74a and the ring electrode 78 and between the lead conductor 74b and the tip electrode 80. Such an embodiment is exemplarily depicted in FIG. 6. As shown, the material 82 is positioned adjacent to both the ring electrode 78 and the tip electrode 80. In such cases, the electrical path between the material 82 and the corresponding electrodes 78 and 80 is not long enough for dangerous electrical potentials to be induced from the MRI fields.

In certain embodiments, the material 82 is part of an assembly 90. For example, in certain embodiments, the material 82 can be hermetically sealed in insulating material 88 similar to that described above with respect to the FIG. 5. As should be appreciated, the material 82 can be formed or molded as desired. In certain embodiments, the material 82 is obtained already pre-shaped. In turn, the insulating material 88 can be provided so as to cover (e.g., coat) the material 82 except for input and output electrical connections similar to that described above with respect to FIG. 5. Another exemplary assembly, in certain embodiments, may involve the material 82 being included as a part of a discrete thermistor, as further discussed below. It should be appreciated that the electrode assembly lead design (of FIG. 5) would provide a more compact design, though also a more sophisticated design over other lead designs having separately positioned elements (depicted in FIG. 6). One skilled in the art would understand the functioning of the material 82 within such other lead designs based on the description provided above with respect to FIG. 5. As such, the functioning of the material 82 in such lead designs is not further described.

Much of the foregoing description has been concerned with describing lead design configurations that can be provided in utilizing the thermally sensitive material 82. As mentioned above, the thermally sensitive material 82 can be configured to exhibit high impedance in the presence of unsafe currents. This will limit patient tissue heating. With respect to the material 82, in certain embodiments, a positive temperature coefficient (PTC) material can be used, as described below.

As is known, a PTC material can be commonly incorporated in thermistors. Thermistors, when placed in an electrical circuit, generally provide a changing resistance with changing temperature of the device. When a PTC material is incorporated in a thermistor, such a PTC thermistor will demonstrate a sharply increased resistance with increased temperature from a transition temperature. PTC materials are commonly known and commercially available, such as barium titanate or barium titanate based materials. The resistance/temperature characteristic of the PTC material, whereby the material abruptly transitions to a high impedance state following such temperature increase from a transition temperature, enables the material to be used in preventing the passage of unsafe currents there through. While PTC materials are specifically discussed herein, it should be appreciated that any material exhibiting a resistance/temperature characteristic similar to that of PTC material would likewise fall within the spirit of the invention.

In use, a PTC thermistor can be configured to exhibit low resistance for currents at or below a design point and dramatically higher resistances at currents beyond the design point. While the PTC material rises in temperature due to such design currents being passed through the material, this rise in temperature translates only in a slight increase to the resistance of the material. As such, the PTC thermistor generally exhibits adequate electrical conductivity for such design current levels. However, if the current flowing into the thermistor exceeds the design levels, the temperature of the PTC material will rise above the transition point. As a result, the electrical resistance of the PTC material will dramatically increase, preventing excessive current from excessively heating body tissue. However, when the high potential current source is removed, the PTC material cools and returns to its low resistance state, from which design currents can be passed through the PTC thermistor.

Figure 7:
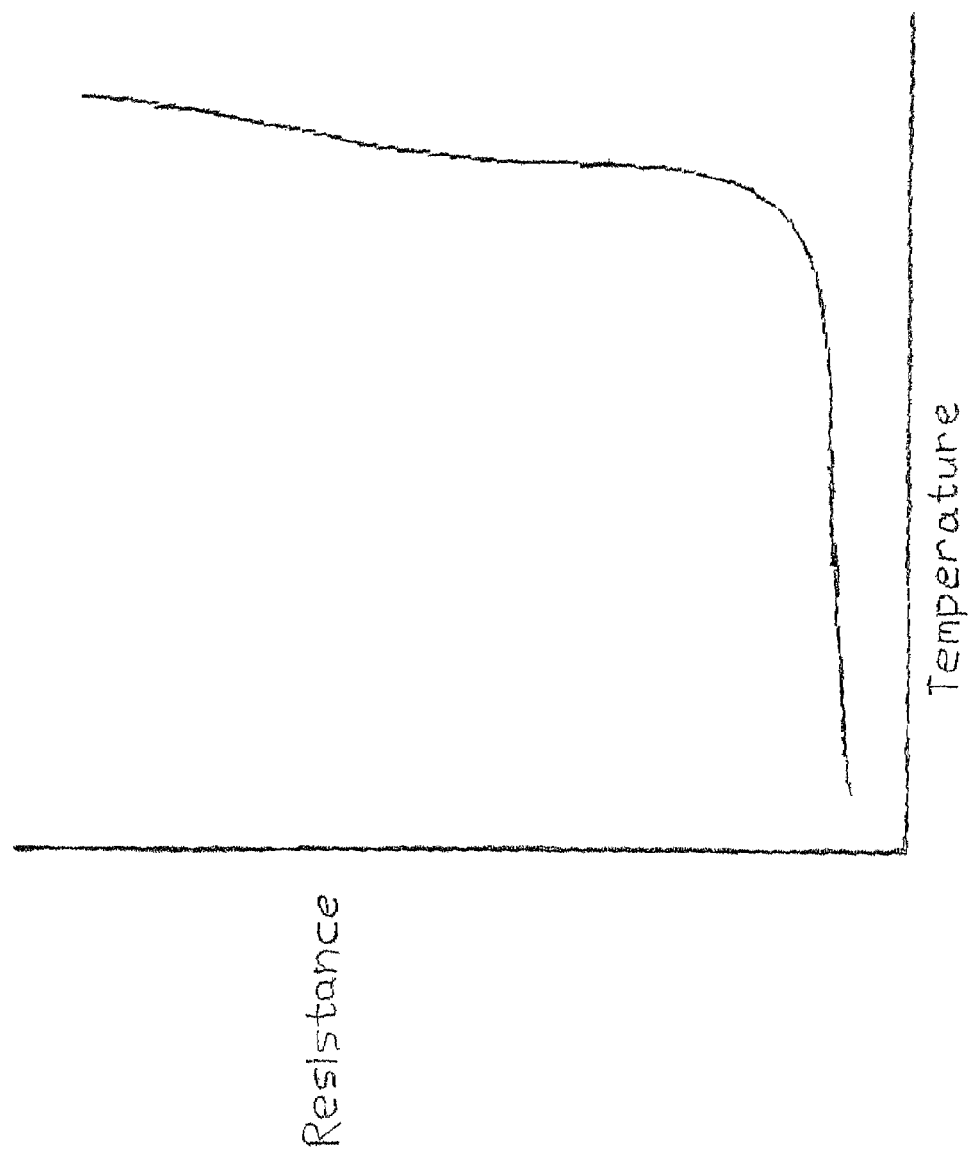
FIG. 7 is a plot exemplarily showing a resistance versus temperature relationship for a typical positive temperature coefficient (PTC) material.

The above-described relationship is illustrated in FIG. 7, which shows a resistance versus temperature relationship for a typical PTC thermistor material.

Several advantages have been found in using PTC material as the thermally sensitive material 82 described above with respect to the lead designs of FIGS. 4 and 5. One advantage in using the PTC material is that it is not frequency sensitive during times at which it is preventing flow of unsafe currents to the patient. In particular, when the PTC material increases in temperature past its "transition temperature" (as further described below), the dielectric constant of the material is found to significantly drop (e.g., from about 1000 to about 1). In turn, capacitive coupling through the PTC material to the electrodes would not be significant at any of the frequencies generally associated with MRI machines. As such, the PTC material can be used with any MRI machine. Another advantage is that for small increases in temperature, the resistance of the PTC material increases by orders of magnitude. There is no thermal lag for the PTC material because it is the temperature of the PTC material that induces the impedance transition, not the temperature of the adjacent tissue. Consequently, any current flowing into the PTC material is prevented from flowing through the electrode and potentially causing damage to body tissue adjacent or proximate to the electrode.

A further advantage is that the PTC material can be precisely adjusted with respect to the temperature at which its resistivity increases by large orders of magnitude, referenced herein as the "transition temperature". Accordingly, this enables the PTC material to be highly adaptable for use in body-implantable environments. For example, normal body temperature is 37° C. (or 98.6° F.). As such, the PTC material can be selected to have a "transition temperature" higher than 37° C. activation temperature (accounting for higher internal body temperatures of body tissue proximate to the PTC material as well as the temperature increase of PTC material for currents higher than nominal or desirable levels). In certain embodiments, this "transition temperature" can be about 40° C. (or 104° F.). Another advantage is that PTC thermistor materials having such a 40° C. "transition temperature" are commercially available, making such materials less costly and readily available. Furthermore, with respect to using the insulating material 88 to generally encase the thermally sensitive material 82, as illustrated in FIG. 5, the material 88 functions in further making the material 82 less susceptible to the surrounding body tissue cooling the material 82. As a result, the PTC system is permitted to be more sensitive to electrical current levels and less sensitive to the precision of the transition temperature of the PTC material. In addition, the material 82 is less apt to transmit its heat to the patient's tissue (via the outer contact 84). As a result, such a design is highly effective in maintaining the functionality of the thermally sensitive material 82 during operation of the conductor lead 74*a* and corresponding electrode 78, while also preventing heating of the patient's tissue proximate to the electrode 78.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. An electrical lead, comprising:
    a conductor assembly having one or more conductors;
    an electrode in electrical communication with one of the conductors, the electrode having an outer contact adapted for contacting adjacent body tissue of a patient; and
    a thermally sensitive material integrated with the electrode in forming an assembly, the thermally sensitive material being completely encased within the electrode and being electrically connected between the one conductor and the electrode outer contact so that current from the one conductor flows through a substantial portion of the thermally sensitive material in order to reach the outer contact, the thermally sensitive material configured to exhibit high impedance in the presence of currents considered unsafe to the patient, thereby preventing the unsafe currents from flowing through the substantial portion of the thermally sensitive material and through the electrode outer contact potentially causing the adjacent body tissue to increase in temperature to an unsafe level, the unsafe currents causing the thermally sensitive material to increase in temperature, thereby causing the material to transition to a high impedance state.

2. The electrical lead of claim 1, wherein the thermally sensitive material comprises positive temperature coefficient material.

3. The electrical lead of claim 1, wherein the thermally sensitive material is electrically connected in series between the one conductor and the electrode outer contact.

4. The electrical lead of claim 1, wherein the thermally sensitive material is sized so as to be internally positioned within the electrode outer contact.

5. The electrical lead of claim 4, wherein the assembly further includes an insulating material enclosing a majority of an outer surface of the thermally sensitive material, the insulating material hermetically sealing the thermally sensitive material within the electrode.

6. The electrical lead of claim 1, wherein the one conductor is electrically coupled to a proximal end portion of the thermally sensitive material and the electrode outer contact is electrically coupled to a distal end portion of the thermally sensitive material, wherein a conductive path between the one conductor and the electrode outer contact is established across the substantial portion of the thermally sensitive material.

7. The electrical lead of claim 6, wherein the assembly further comprises an insulating material enclosing a majority of an outer surface of the thermally sensitive material, thereby enhancing the conductive path between the one conductor and the electrode outer contact across the thermally sensitive material.

8. The electrical lead of claim 1, wherein the electrode further includes an inner contact, the electrode inner contact electrically connecting the one conductor to the thermally sensitive material.

9. The electrical lead of claim 8, wherein the assembly further comprises an insulating material that surrounds the thermally sensitive material except for locations in which the electrode outer contact and the electrode inner contact are in electrical contact with the thermally sensitive material.

10. An electrode, comprising:
    an outer contact adapted for contacting adjacent body tissue of a patient;
    an inner contact adapted for electrical coupling to a lead conductor; and
    a thermally sensitive material electrically connected between the inner contact and the outer contact so that current from the one conductor flows through a substantial portion of the thermally sensitive material in order to reach the outer contact, the thermally sensitive material forming an assembly with the outer contact and inner contact whereby the thermally sensitive material is completely encased, the thermally sensitive material configured to exhibit high impedance in the presence of currents considered unsafe to the patient, thereby preventing the unsafe currents from flowing through the substantial portion of the thermally sensitive material and through the outer contact potentially causing the adjacent body tissue to increase in temperature to an unsafe level, the unsafe currents causing the thermally sensitive material to increase in temperature, thereby causing the material to transition to a high impedance state.

11. The electrode of claim 10, wherein the thermally sensitive material comprises positive temperature coefficient material.

12. The electrode of claim 10, wherein the thermally sensitive material is electrically connected in series between the inner contact and the outer contact.

13. The electrode of claim 10, wherein the thermally sensitive material is sized so as to be internally positioned within the outer contact.

14. The electrode of claim 10, wherein the inner contact is electrically coupled to a proximal end portion of the thermally sensitive material and the outer contact is electrically coupled to a distal end portion of the thermally sensitive material, wherein a conductive path between the inner contact and the outer contact is established across the substantial portion of the thermally sensitive material.

15. The electrode of claim 13, further comprising an insulating material enclosing a majority of an outer surface of the thermally sensitive material, the insulating material hermetically sealing the thermally sensitive material between the inner contact and the outer contact.

16. A method of providing an electrical lead configured to prevent currents considered unsafe to a patient, comprising:
    providing a conductor assembly having one or more conductors;
    providing an electrode in electrical communication with one of the conductors, the electrode having an outer contact adapted for contacting adjacent body tissue of a patient;
    integrating a thermally sensitive material with the electrode to form an assembly such that the thermally sensitive material is completely encased within the electrode; and
    electrically connecting the thermally sensitive material between the one conductor and the electrode outer contact so that current from the one conductor flows through a substantial portion of the thermally sensitive material in order to reach the electrode outer contact, the thermally sensitive material configured to exhibit high impedance in the presence of currents considered unsafe to the patient, thereby preventing the unsafe currents from flowing through the substantial portion of the thermally sensitive material and through the electrode outer contact potentially causing the adjacent body tissue to increase in temperature to an unsafe level, the unsafe currents causing the thermally sensitive material to increase in temperature, thereby causing the material to transition to a high impedance state.

17. The method of claim 16, wherein the thermally sensitive material upon reaching a certain temperature exhibits significant increased resistance upon further increases in temperature.

18. The method of claim 16, wherein the thermally sensitive material is electrically connected in series between the one conductor and the electrode outer contact.

19. The method of claim 16, wherein the thermally sensitive material is sized so as to be internally positioned within the electrode outer contact.

20. The method of claim 19, wherein the assembly further includes an insulating material enclosing a majority of an outer surface of the thermally sensitive material, the insulating material hermetically sealing the thermally sensitive material within the electrode.

21. The method of claim 16, wherein the one conductor is electrically coupled to a proximal end portion of the thermally sensitive material and the electrode outer contact is electrically coupled to a distal end portion of the thermally sensitive material, wherein a conductive path between the one conductor and the electrode outer contact is established across the substantial portion of the thermally sensitive material.

22. The method of claim 21, wherein the assembly further comprises an insulating material enclosing a majority of an outer surface of the thermally sensitive material, thereby enhancing the conductive path between the one conductor and the electrode outer contact across the thermally sensitive material.

23. The method of claim 16, wherein the electrode further includes an inner contact, the electrode inner contact electrically connecting the one conductor to the thermally sensitive material.

24. The method of claim 23, wherein the assembly further comprises an insulating material that surrounds the thermally sensitive material except for locations in which the electrode outer contact and the electrode inner contact are in electrical contact with the thermally sensitive material.

25. An electrical lead, comprising:
a conductor assembly having one or more conductors;
an electrode in electrical communication with one of the conductors, the electrode having an outer contact adapted for contacting adjacent body tissue of a patient; and
a positive temperature coefficient material integrated with the electrode in forming an assembly, the positive temperature coefficient material being completely encased within the electrode and being electrically connected between the one conductor and the electrode outer contact so that current from the one conductor flows through a substantial portion of the positive temperature cofficient material in order to reach the electrode outer contact, the positive temperature coefficient material integrated into an assembly with the electrode, the positive temperature coefficient material configured to exhibit high impedance in the presence of currents considered unsafe to the patient, thereby preventing the unsafe currents from flowing through the substantial portion of the positive temperature coefficient material and through the electrode outer contact potentially causing the adjacent body tissue to increase in temperature to an unsafe level, the unsafe currents causing the positive temperature coefficient material to increase in temperature, thereby causing the material to transition to a high impedance state.

26. The electrical lead of claim 25, wherein the positive temperature coefficient material is electrically connected in series between the one conductor and the electrode outer contact.

27. The electrical lead of claim 25, wherein the positive temperature coefficient material is sized so as to be internally positioned within the electrode outer contact.

28. The electrical lead of claim 25, wherein the one conductor is electrically coupled to a proximal end portion of the positive temperature coefficient material and the electrode outer contact is electrically coupled to a distal end portion of the positive temperature coefficient material, wherein a conductive path between the one conductor and the electrode outer contact is established across the substantial portion of the positive temperature coefficient material.

29. The electrical lead of claim 28, wherein the assembly further comprises an insulating material enclosing a majority of the outer surface of the positive temperature coefficient material, thereby enhancing the conductive path between the one conductor and the electrode outer contact across the positive temperature coefficient material.

30. The electrical lead of claim 27, wherein the assembly further includes an insulating material enclosing a majority of an outer surface of the positive temperature coefficient material, the insulating material hermetically sealing the thermally sensitive material within the electrode.

* * * * *